(12) United States Patent
Cristoforo

(10) Patent No.: US 9,053,626 B2
(45) Date of Patent: Jun. 9, 2015

(54) PROGRAMMABLE CARBON MONOXIDE SAFETY DEVICE

(75) Inventor: Michael Cristoforo, Palm City, FL (US)

(73) Assignee: Daydream Believers, LLC, Palm City, FL (US)

(*) Notice: Subject to any disclaimer, the term of this patent is extended or adjusted under 35 U.S.C. 154(b) by 558 days.

(21) Appl. No.: 13/462,408

(22) Filed: May 2, 2012

(65) Prior Publication Data

US 2012/0310547 A1 Dec. 6, 2012

Related U.S. Application Data

(60) Provisional application No. 61/481,298, filed on May 2, 2011, provisional application No. 61/521,429, filed on Aug. 9, 2011.

(51) Int. Cl.
*G06F 19/00* (2011.01)
*G08B 21/14* (2006.01)

(52) U.S. Cl.
CPC .................................. *G08B 21/14* (2013.01)

(58) Field of Classification Search
CPC . G01N 27/12; G01N 33/004; G01N 33/0047; G01N 21/61; G01N 27/124; G01N 27/26; G01N 27/64; G01N 33/0065; G08B 21/14
USPC ........... 702/23, 24, 31, 54, 62, 93; 123/179.2; 340/521, 531, 606, 632, 870.16; 454/195, 239, 343; 701/29, 211
See application file for complete search history.

(56) References Cited

U.S. PATENT DOCUMENTS

| | | | |
|---|---|---|---|
| 3,826,180 A | 7/1974 | Hayashi | |
| 4,197,675 A | 4/1980 | Kelly | |
| 4,360,801 A | 11/1982 | Duhame | |
| 4,819,551 A | 4/1989 | Vole | |
| 5,576,739 A | 11/1996 | Murphy | |
| 5,947,814 A | 9/1999 | Czeck et al. | |
| 6,025,788 A * | 2/2000 | Diduck | 340/870.16 |
| 6,036,595 A | 3/2000 | Vole | |
| 7,650,864 B2 * | 1/2010 | Hassan et al. | 123/179.2 |
| 2002/0111132 A1 | 8/2002 | Meneely, Jr. | |
| 2003/0020619 A1 | 1/2003 | Winters et al. | |
| 2003/0087600 A1 | 5/2003 | Meneely, Jr. | |
| 2004/0078124 A1 * | 4/2004 | Schauble | 701/29 |
| 2005/0212681 A1 | 9/2005 | Dzurko et al. | |
| 2006/0202815 A1 * | 9/2006 | John | 340/531 |
| 2007/0146150 A1 | 6/2007 | Calabrese et al. | |
| 2007/0182574 A1 | 8/2007 | Dzurko et al. | |
| 2007/0255493 A1 * | 11/2007 | Ayoub et al. | 701/211 |
| 2009/0005917 A1 | 1/2009 | Hole | |
| 2010/0201531 A1 | 8/2010 | Pakravan et al. | |
| 2011/0248856 A1 * | 10/2011 | Obenchain | 340/606 |

* cited by examiner

*Primary Examiner* — John H Le
(74) *Attorney, Agent, or Firm* — Mchale & Slavin P.A.

(57) ABSTRACT

A programmable toxic gas safety device for detecting a toxic gas, such as carbon monoxide, is provided. The programmable safety device is preferably used in an enclosed area for monitoring the levels of gas emitted by a device that can produce a toxic gas. The device contains a controller which is operably coupled to at least one transmitter and at least one sensor for sensing the level of the toxic gas in the enclosed area, and is operable to provide a signal to remotely operate the toxic gas producing device. The device further contains one or more receivers for learning a command signal which actuates a specific functionality to the toxic gas producing device.

18 Claims, 16 Drawing Sheets

PROGRAMMABLE CARBON MONOXIDE SAFETY DEVICE

CROSS REFERENCE TO RELATED APPLICATIONS

This application claims priority under 35 USC 119(e) to the U.S. Provisional Patent Application No. 61/481,298, filed May 2, 2011, entitled, "Programmable Carbon Monoxide Safety Device", and U.S. Provisional Patent Application No. 61/521,429, filed Aug. 9, 2011, entitled, "Programmable Carbon Monoxide Safety Device", the contents of which are incorporated herein in their entirety.

FIELD OF THE INVENTION

The present invention relates to a device and system for preventing harmful effects of toxic gaseous build-up; and more particularly, to a device and system for preventing an individual from succumbing to the harmful effects of excessive levels of carbon monoxide produced from a motor vehicle stored in an enclosed space.

BACKGROUND OF THE INVENTION

Carbon monoxide poisoning is a potentially life threatening situation which occurs by the inhalation of carbon monoxide (CO). In general, red blood cells are responsible for delivering oxygen to cells and tissues for normal functioning. In the presence of carbon monoxide, the red blood cells tend to pick up carbon monoxide molecules at a faster rate than oxygen molecules. Therefore, given a large presence of carbon monoxide molecules, the body replaces oxygen with carbon monoxide, resulting in damage to the cells and tissues and significant toxicity to the central nervous system. Carbon monoxide poisoning manifests with the symptoms of headache, dizziness, weakness, nausea, vomiting, chest pain, and confusion. Given that these symptoms are generally not associated with fatal disease statistics and mimic other common illnesses, it is difficult for patients to recognize and harder for doctors to diagnosis. If not treated properly and immediately, carbon monoxide poisoning is fatal.

Carbon monoxide is an odorless, colorless, tasteless, and non-irritating gas. Because of its difficulty in detection, it is not surprising that a significant number of deaths have been attributed to carbon monoxide poisoning. For a time period between the years 1979 and 1988, over 56,000 deaths were listed as having carbon monoxide as a contributing cause. Of those 56,000 cases, 46% (approximately 25,900 people) were categorized as a suicide and 21% (approximately 11,500 people) were categorized as unintentional. From 1999 until 2004, 16,400 deaths were attributed to carbon monoxide poisoning, with 16% (approximately 2,650) categorized as unintentional. While the numbers have decreased over the last decade, it is estimated that nearly 2,000 Americans will die as a result of intentional carbon monoxide poisoning, as well as another 400 Americans will die each year from unintentional poisoning. More importantly, given the new technology to operate vehicles remotely, this number is expected to increase.

Common sources of carbon monoxide include heating and cooking equipment, blocked fireplaces, and furnaces. Furnaces, for example, may be installed at various areas within a home such as the basement, the attic or within a closet. Any of these installations could infiltrate the house with carbon monoxide in the event of a malfunction. A mechanical failure, such as a fractured heat exchanger, may force carbon monoxide through the duct-work of the house to create a toxic condition. Another common source of carbon monoxide in residential settings is motor vehicles. Automobiles, for example, produce carbon monoxide that can reach dangerous levels when left running in a closed or poorly ventilated garage. It is not uncommon for the carbon monoxide in the garage to infiltrate the attached home. Should such an event occur while the unit occupants are sleeping, fatal consequences may result.

Common methods for minimizing carbon monoxide result from two primary mechanisms. The first mechanism relies on knowledge and vigilance. When installing devices that could produce carbon monoxide, it is advisable that such devices are used and installed by professionals in accordance with the manufacture's instructions. Use of portable generators and other portable fuel burning devices are strongly discouraged in an enclosed area such as the home, garage, or other part of a residential space. While such steps are important to minimize the risk of carbon monoxide leaks, the only way to know if the home contains undesirable levels of carbon monoxide is through installation of carbon monoxide detectors. Typically, carbon monoxide detectors are coupled to an audible alarm in order to alert the homeowner that the levels of carbon monoxide are dangerous and action must be taken. To be effective, therefore, the user must be able to hear the audible alarm and be capable of exiting the contaminated area.

DESCRIPTION OF THE PRIOR ART

Carbon monoxide detectors, whether battery operated, plug-ins which plug directly into the electrical outlets in a wall, or those detectors directly hardwired into the home's wiring, are known in the art and commercially available. Many of these devices are effective if the homeowner replaces the batteries or keeps the device plugged into the wall outlet. Devices that are hardwired into the user's home may not require the homeowner to care for the device as much as battery operated or plug-ins, but hardwired devices can be expensive, not easily installed, and can fail should the power to the home be disrupted. More importantly, most carbon monoxide detectors that are currently sold use passive means for minimizing the harm from increasing levels of carbon monoxide in an enclosed area. Once the sensors sense a predetermined level of carbon monoxide, the device activates and sounds an alarm. If the alarm signal is heard, it is up to the user to avoid harm by exiting the area. Failure to hear the alarm or failure for the audible signal to trigger results in the homeowner being unaware of the mounting danger. Moreover, some individuals can not remove themselves from the danger, either because they are incapacitated as a result of the carbon monoxide fumes or have pre-existing physically impairments that make it difficult or impossible to escape.

There have been attempts in the art to improve the performance of carbon monoxide detectors by causing them to open garage doors, operate fans or turn off devices that are producing carbon monoxide. For example, U.S. Pat. No. 3,826,180 discloses a ventilation fan system with smoke detector speed control. The device includes an electronic circuit that is actuated when a detecting element detects the existence of any smoke or gas in an enclosed area while a fan is in a manually selected slow rotating mode of operation or in a stand-by stopped position. Upon detection of smoke or a gas such as carbon monoxide, the fan is automatically put into full rotation mode in order to expel the smoke or gas. The device expels the smoke or gas through a window that includes solenoid operated shutters that are also controlled by the device.

U.S. Pat. No. 4,197,675 discloses a sensing system for use in a garage or other similar enclosure having an automatic door operator for automatically opening a garage door responsive to a lack of sufficient oxygen therein. The device includes a gas detector located within the enclosure responsive to actuate a detection relay which in turn will close a normally open detection switch. The closing of the detection switch causes operation of the door opener to allow oxygen to enter into the enclosure through the door opening.

U.S. Pat. No. 4,360,801 discloses a home security and garage door operation system. The system includes a gas sensor for detecting the level of toxic gas in the garage. When the gas level exceeds a predetermined threshold, the garage door is automatically opened.

U.S. Pat. No. 4,819,551 discloses a safety system for smoke and fumes. The system includes a detector unit for detecting fumes, including carbon monoxide. The device is located in a garage, and circuitry controlled thereby automatically opens the garage door, or operates an exhaust blower, or both upon detection of carbon monoxide.

U.S. Pat. No. 5,576,739 discloses a carbon monoxide safety system. The system measures noxious gas concentration in an affected space, and controls the device producing the noxious gas for decreasing the concentration of the gas in the affected space. The invention is particularly described in relation to measuring carbon monoxide concentration in an automobile garage, and for controlling the garage door opener circuit to open the garage door in response to a preselected concentration of carbon monoxide. Also described is a system for deactivating a furnace operating circuit to turn off the furnace in the event of excessive carbon monoxide concentration.

U.S. Pat. No. 5,947,814 discloses a garage carbon monoxide venting system. The gas venting system includes an electrically operated exhaust fan used in an enclosed garage to expel unwanted gases, especially carbon monoxide, to outside the garage and away from an attached residence.

U.S. Pat. No. 6,036,595 discloses a safety system for smoke and fumes. The safety system includes a hard wired carbon monoxide detector that includes a heater system for providing accurate carbon monoxide sensing in harsh environments. The carbon monoxide detector is hard wired to the garage door opener to cause the garage door to open in the event that a high level of carbon monoxide is detected in the garage.

U.S. Patent Publication Nos. 2002/0111132 and 2003/0087600 disclose a carbon monoxide ventilation system comprising a carbon monoxide sensor, a fan, and a vent. The carbon monoxide sensor supplies power to the fan when a threshold level of carbon monoxide is detected. The fan includes a motor and a propeller which draws air into the fan unit, and expels the air through the vent.

U.S. Patent Publication No. 2003/0020619 discloses a proactive carbon monoxide protection system that includes a carbon monoxide detector connected to a control module adapted to turn off the source of carbon monoxide, sound a central alarm, and alert an off-site monitoring station upon detection of carbon monoxide by the detector.

U.S. Patent Publication No. 2005/0212681 discloses a garage monitoring system for use with an automatic garage door opening mechanism that includes a carbon monoxide detector configured to sense the presence of carbon monoxide within the garage and generate an audible alarm when carbon monoxide reaches a predetermined level in the garage.

U.S. Patent Publication No. 2010/0201531 discloses a carbon monoxide detection apparatus having one or more sensors which are connected to an appliance, such as a furnace or water heater. The device contains sensors which are designed to detect CO levels and activate the appliance cut-off switch should the levels of carbon monoxide become too high.

Despite these improvements, injury from automobile related carbon monoxide production remains problematic. Although many of the above described devices can be programmed to shut off devices in the home or open a garage door, exposure from automobiles remains a threat. Technological advances allow automobile owners the ability to remotely start their cars and for motor vehicle operation without the use of keys. While these new abilities provide comfort and ease to automobile users, they also provide increased opportunities for carbon monoxide poisoning. Moreover, devices that allow for remote functioning can be programmed to operate multiple vehicles or other appliances, thereby increasing the risk of starting one vehicle when a second vehicle, or other appliance, was the intended target. If the user is not aware of the fact that they inadvertently turned on the wrong vehicle, or the vehicle instead of the appliance, that vehicle can be left with the engine running for an indefinite time period. In addition, different remote start devices can be programmed to operate a single vehicle. Such actions increase the risk of carbon monoxide poisoning if a remote user inadvertently turns on the car while it is in the garage; while others, who are unaware of the car being started, remain in the home.

Additionally, hybrid cars which use a combination electric motor and internal combustion engine have become more popular as a result of rising fuel costs. When the car is using its electric motor, it is much quieter than the traditional internal combustion engines. Since the internal combustion engine is not operating, this provides an opportunity for a driver to park their car in their garage, place in it park, and forget to turn off the vehicle. Typical hybrid cars are capable of switching power sources so that when the electric motor no longer has power, it automatically switches to using the internal combustion engine. For the car owner who parked their hybrid car in the garage and did not realize that the car was still running, they face the danger of carbon monoxide poisoning as the hybrid car switches to operating on the internal combustion engine.

Therefore, what is needed in the art is an improved programmable, carbon monoxide detector which can be used to sense carbon monoxide levels within an enclosed area and can be programmed to turn off the source of the carbon monoxide, i.e. cut off the automobile's engine, should levels of carbon monoxide become dangerous.

SUMMARY OF THE INVENTION

The instant invention describes a programmable toxic gas safety device for detecting a toxic gas such as carbon monoxide. The programmable safety device is preferably used in an enclosed area which stores a device that can produce the toxic gas. The programmable safety device contains at least one sensor operable to sense the level of the toxic gas in the enclosed area. The device further contains one or more receivers for learning a command code which is specific to one or more external devices that produce the toxic gas. At least one transmitter functions to reproduce the learned command signal in order to actuate the command. A control unit is operably coupled to the transmitter, receiver, and sensor and is operable to provide a signal to operate an external device.

In another embodiment, the carbon monoxide detector is preprogrammed to include at least one command related to a certain vehicle or type of vehicle that can be transmitted to the vehicle. In this embodiment, the vehicle's on-board computer can be programmed (taught) to receive any commands sent from the CO detector in a similar manner to teaching the vehicle an additional key fob, smart key or the like. The preprogramming may include a particular type of encryption, or an algorithm, that is specific to the vehicle or type of vehicle to prevent unwanted persons from intercepting and spoofing the signal.

In yet another embodiment, the carbon monoxide detector includes a transmitter or transceiver that is constructed and arranged to communicate with a vehicle network interface. The vehicle network interface may connect directly to a J2534 or other suitable connector having access to the vehicular on-board computer system. The vehicular network interface includes a receiver or transceiver therein that is compatible with the receiver/transceiver in the carbon monoxide detector. This construction allows shut down engine commands to be transferred to vehicles that do not include smart keys, key fobs or the like installed by the OEM.

In still yet another embodiment, the carbon monoxide detector includes a transmitter/transceiver that can communicate with a cell phone network or cell phone device such as an ONSTAR™ system. This construction allows for a variety of options relating to locating and shutting down the vehicle, as well as providing notice to the vehicle owner that a problem has been detected and action in response thereto may have taken place.

In still yet another embodiment, the carbon monoxide detector includes an FM transmitter having suitable power to broadcast a signal to FM radios positioned within range to notify persons in the vicinity of the vehicle that a dangerous condition exists.

In still yet another embodiment, the carbon monoxide detector is constructed and arranged to communicate a distress call directly to a satellite service provider. The satellite service provider could then communicate directly with the owner of the vehicle via phone, or alternatively could dispatch emergency personnel to the location of the distress call.

In an illustrative example, the programmable safety device is a programmable carbon monoxide safety device that is operable to detect levels of carbon monoxide produced from a motor vehicle stored in a garage. The motor vehicle may have been unintentionally left running or unintentionally been caused to start as a result of a remote start device. In either case, as the car continues to run, the levels of carbon monoxide reach dangerous levels, potentially harming anyone remaining in the car or inside an attached dwelling. As soon as the carbon monoxide levels reach predetermined threshold levels, the carbon monoxide safety device produces a signal which is received by the automobile to turn off the engine, thereby eliminating the continuous production of carbon monoxide.

Accordingly, it is an objective of the instant invention to provide a programmable safety device and system for preventing toxic gas poisoning.

It is a further objective of the instant invention to provide a programmable carbon monoxide safety device and system which minimizes the risk of carbon monoxide poisoning.

It is yet another objective of the instant invention to provide a programmable carbon monoxide safety device and system which minimizes the risk of carbon monoxide poisoning by remotely operating an external device producing the carbon monoxide.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
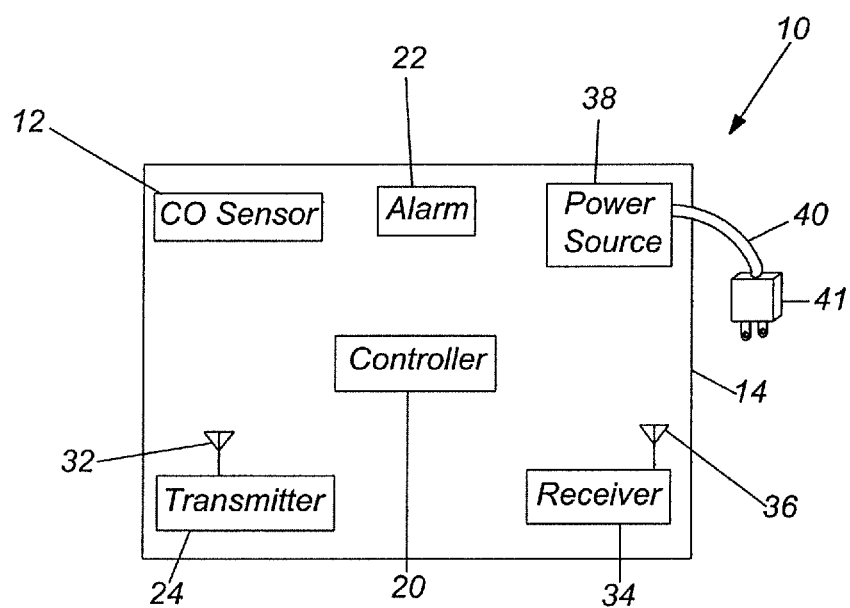
FIG. 1 is a schematic block diagram of an illustrative example of a programmable carbon monoxide device in accordance with the instant invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 2:
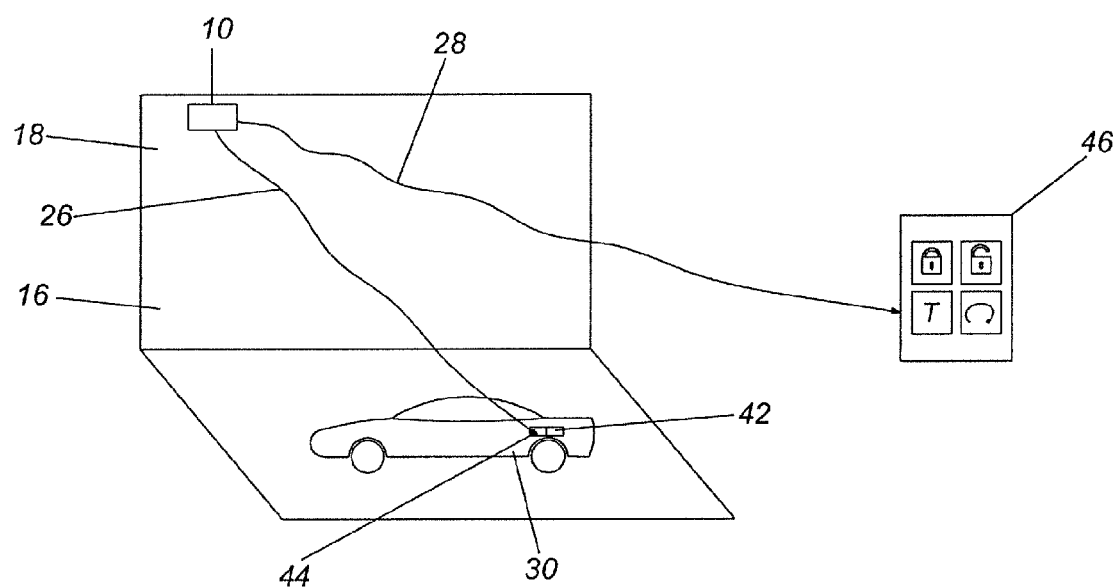
FIG. 2 is a simplified diagram of an illustrative environment for the present invention.

FIG. 1 is a schematic block diagram of an illustrative example of the programmable carbon monoxide safety device 10, including a programmable transmitter and receiver feature. The primary function of the programmable carbon monoxide safety device 10 is to detect levels of carbon monoxide in an enclosed space, and when the level reaches a predetermined threshold, produce a signal that terminates the carbon monoxide producing source. The device 10 therefore contains at least one carbon monoxide sensor 12 coupled to a base module 14. The device 10 is preferably placed in an enclosed area, such as a garage 16, and mounted on the wall 18 or ceiling of the garage, see FIG. 2.

Since the health effects of carbon monoxide depend on the concentration and length of exposure, the sensor 12 can be calibrated to detect various levels of carbon monoxide, and is preferably capable of detecting carbon monoxide levels at extreme temperatures, either hot or cold as well as various levels of humidity. For example, the sensor may have a setting for detection of extremely low levels of carbon monoxide such as 1 to 70 parts per million (ppm) for persons who may have health conditions that may make such levels dangerous to them. Preferably, the sensor is calibrated to detect carbon monoxide levels in the range of 150-400 ppm. Alternately, the programmable carbon monoxide safety device 10 can be calibrated with a time sensitive threshold. For example, the programmable carbon monoxide safety device 10 can be calibrated to respond when the concentration of carbon monoxide in the air is 50 ppm for six hours, 200 ppm for one-half hour or 400 ppm at any time. These specific calibration limits are for illustrative purposes only, and not intended to be limiting. In at least one embodiment, the carbon monoxide detector may be mounted within the confines of the home and a tube or the like may be extended into the garage area for sensing air quality within the garage while the carbon monoxide sensor 12 is maintained within the environment controlled area of the home. This construction provides a controlled climate for the sensor while air quality is measured outside of the climate controlled area.

The programmable carbon monoxide safety device 10 includes a controller 20 for controlling the device 10 functionality. Operably coupled to the controller is a speaker 22, or the like, which produces an audible signal should the sensor 12, which is also operably connected to the controller 20, detect levels of carbon monoxide that exceed its set threshold. Typically, the controller 20 is a microprocessor with memory capability. The programmable carbon monoxide safety device 10 also includes a transmitter 24 constructed and arranged for producing command signals 26, 28 (see FIG. 2) to one or more external devices, such as a motor vehicle 30. Typically, the command signals 26, 28 are radio frequency signals. In addition, signals used by cellular phone technology may be used to transmit the command signals 26, 28 to a smart phone or other external device. The command signal preferably contains a unique frequency, code and/or encryption to operate the external device in a secured manner. The transmitter 24 may include an antenna 32 for broadcasting the command signal.

The programmable carbon monoxide safety device 10 further includes a receiver 34 for receiving wireless control signals, and may optionally include an antenna 36. The receiver 34 is programmable in that it is capable of receiving external device control signals in a learning mode to learn appropriate signals in order to actuate a command signal specific to the external device. The receiver can learn the signal directly from the external device or from a secondary external device, such as a key fob, that can remotely operate the external device. To aid in this functionality, the controller 20 contains memory for learning the command signals. The controller 20 may then command the transmitter 24 to reproduce the learned command signal. Alternatively, the device 10 may be programmed to reproduce more than one unique wireless command signal, thereby operating several external devices. The programmable carbon monoxide safety device 10 also includes a power source 38 which may be a battery and/or an electrical plug 40 extending from the base module 14 which may include an electrical connector 41 suitable for connection to the electrical wiring of a conventional AC power supply grid that is commonly used in a dwelling, such as a wall outlet supplying 120 volts AC.

Figure 3:
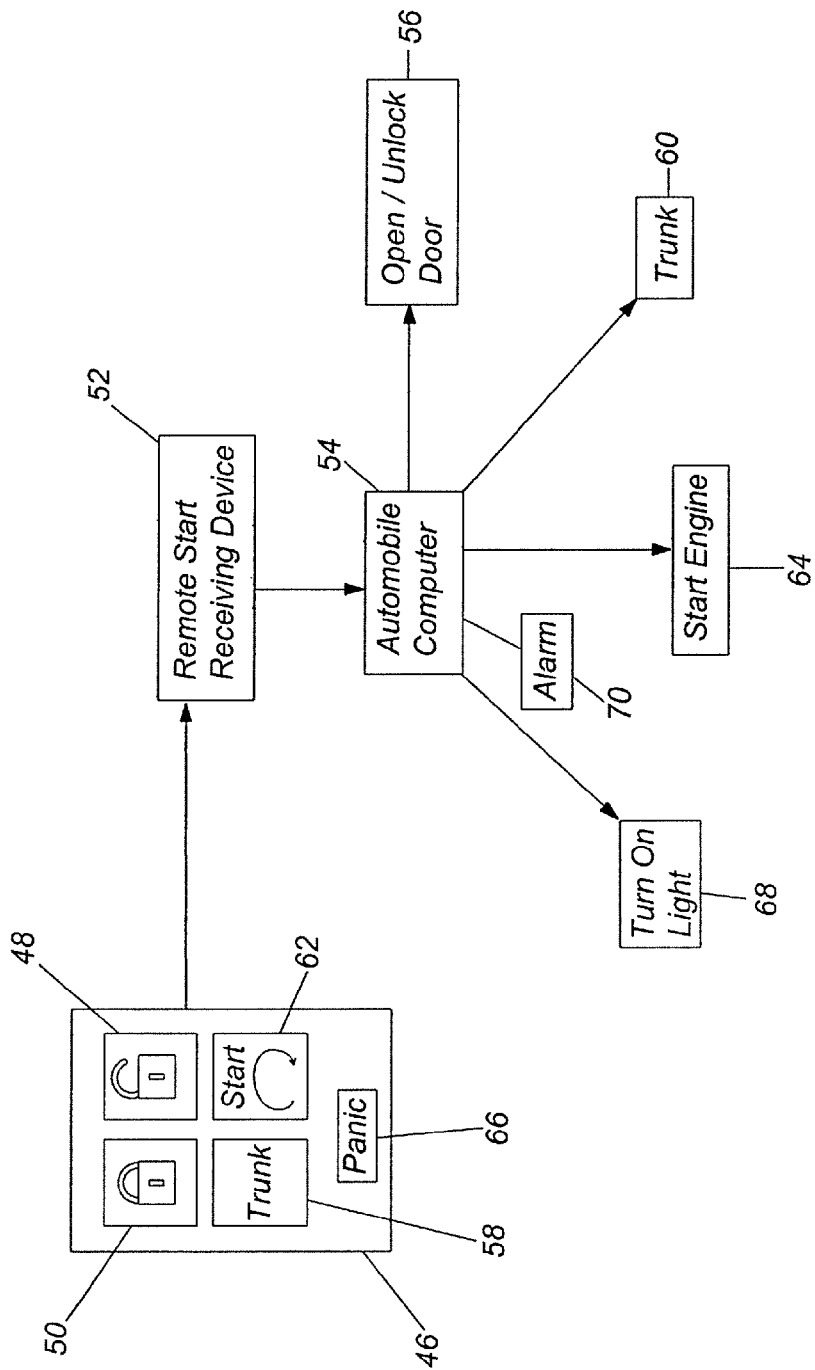
FIG. 3 is a block diagram of a typical keyless automotive remote system of the prior art.

The external devices include, but are not limited to, an on-board computer control unit 20 inside a motor vehicle 30, a remote start receiving device 44, such as those sold by VIPER, smart devices 46, such as smart phones including APPLE's iPHONE or BLACKBERRY devices, or a keyless remote device, such as key fobs, smart keys or remote controls (not illustrated). Referring to FIG. 3, the smart device 46 is illustrated as having keyless remote capabilities. For example, the typical keyless remote device contains control commands, either a push down button (not illustrated), or touch screen technology (such as the technology used with APPLE's iPHONE) to actuate a command. The smart device 46 illustrated in FIG. 3 shows a plurality of automobile related remote commands. Touching area 48 or 50 sends a signal to a remote starter receiving device 52 installed in motor vehicle 30. The signal may then be sent to the motor vehicle's on-board computer system 54 to remotely lock/unlock 56 the door. Engaging area 58 remotely opens the motor vehicle's trunk 60. Engaging area 62 remotely starts the engine 64 of motor vehicle 30. Other remote commands 66 may be utilized to perform other functions, such as turning on the motor vehicle's lights 68 or engaging an audible alarm 70.

Figure 4:
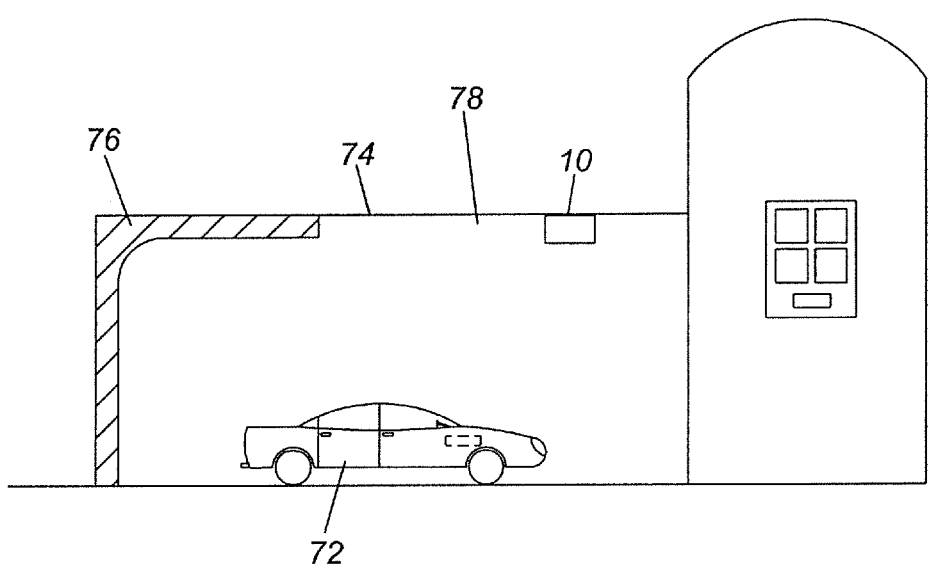
FIG. 4 is a simplified diagram of an illustrative environment for the present invention, illustrating an automobile in the off position in a garage.

FIGS. 4-9 show an illustrative example of how the programmable carbon monoxide safety device 10 is used. As described herein, the programmable carbon monoxide safety device 10 is a carbon monoxide detector, but it is understood that the invention can also be used with sensors of other noxious or toxic gases without departing from the scope of the invention. Additionally, the invention is described as being used in a residential garage, but it is understood that the invention can beneficially be used in other spaces, such as auto repair facilities, workshops, parking garages and the like where there is a danger of accumulating high levels of carbon monoxide or other gases without departing from the scope of the invention. Referring specifically to FIG. 4, automobile 72 is parked in an enclosed area depicted as a garage 74 with garage door 76 in the closed position. The programmable carbon monoxide safety device 10 is placed on the wall 78 of garage 74. In the parked position, the automobile 72 is not at risk for producing carbon monoxide as the engine is in the off position. Although no harmful levels of carbon monoxide are being emitted, the programmable carbon monoxide safety device 10 is sensing for any build-up.

Figure 5:
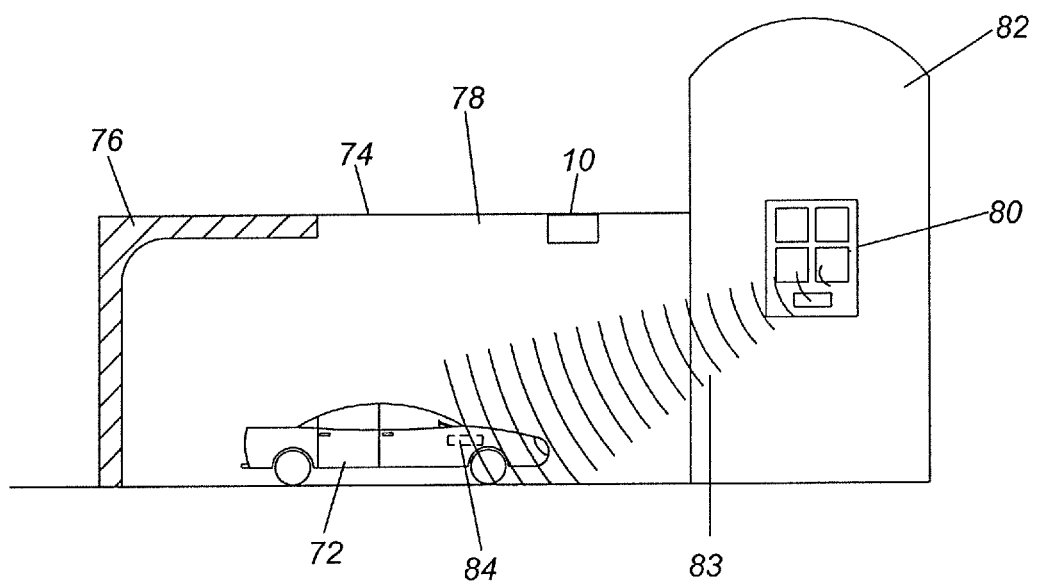
FIG. 5 is a simplified diagram of an illustrative environment for the present invention, illustrating remote activation of the automobile's engine.
Figure 6:
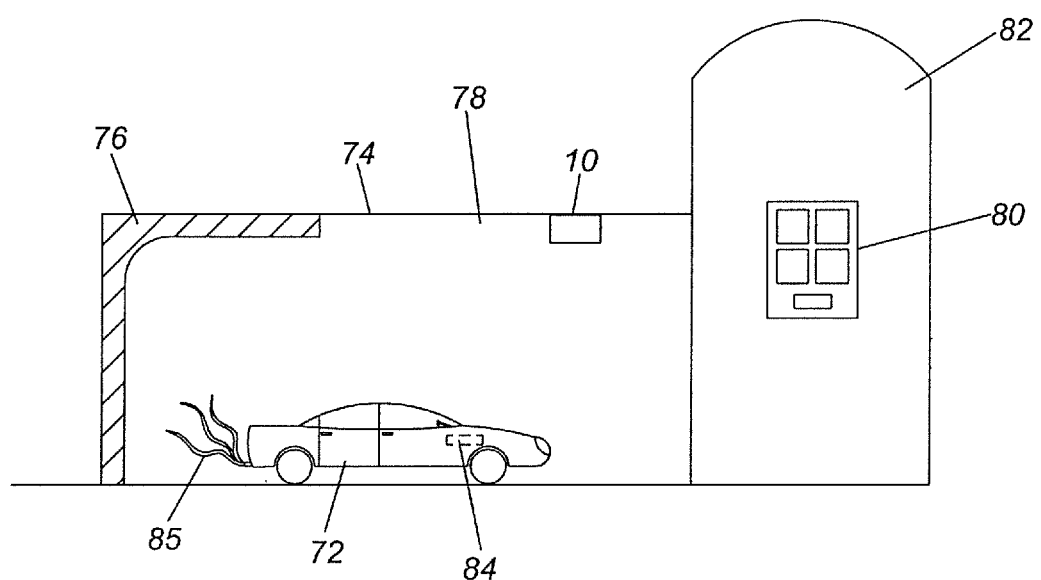
FIG. 6 is a simplified diagram of an illustrative environment for the present invention, illustrating carbon monoxide emission.

FIG. 5 illustrates the automobile 72 in the parked position, but with the engine running. In this position, carbon monoxide is being produced in the enclosed area and not properly vented. The ignition has been turned on by use of a remote keyless device, such a remote start key fob, or as illustrated an iPHONE 80 having remote start capability. The iPHONE is typically stored remotely from the automobile 72, such as in the house 82 attached to the garage 74. The iPHONE 80 sends a command signal 83 to the automobile's remote start device 84, which starts the automobile's engine. As described herein, the automobile 72 has been turned on from a remote starter, however, it is understood that the invention can also be used in the situation in which the user of automobile 72 places the car in the garage and forgets to turn off the engine. In either case, because the automobile 72 is running, carbon monoxide 85 is being emitted, see FIG. 6. Since the automobile 72 has just begun to emit carbon monoxide, the levels are not sufficient to trigger the programmable carbon monoxide safety device 10.

Figure 7:
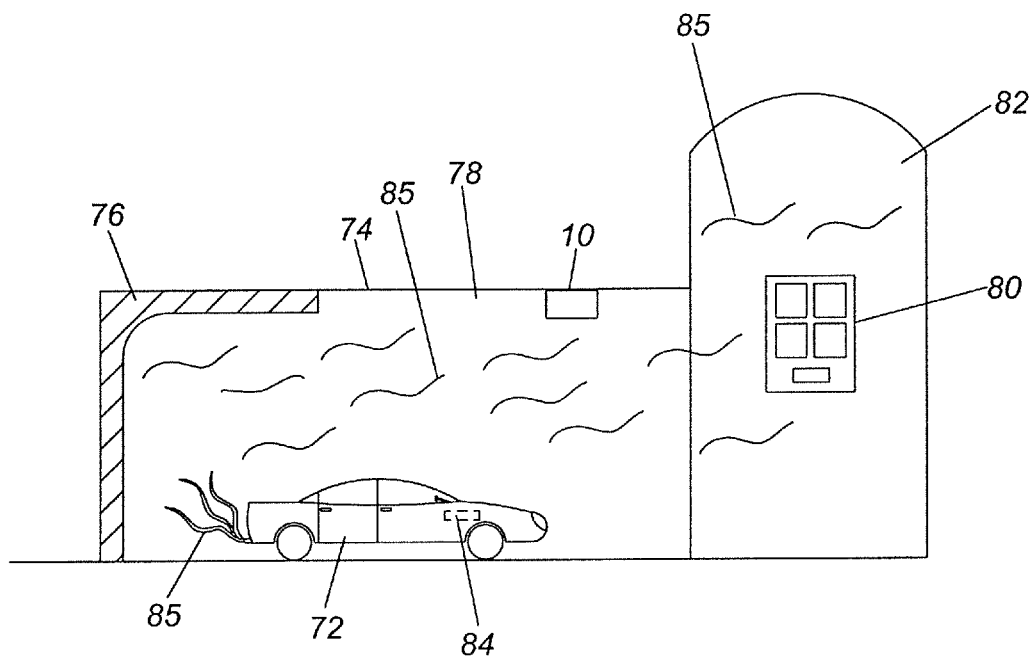
FIG. 7 is a simplified diagram of an illustrative environment for the present invention, illustrating enhanced levels of carbon monoxide emissions and detection of such levels by the programmable carbon monoxide safety device in accordance with the present invention.
Figure 8:
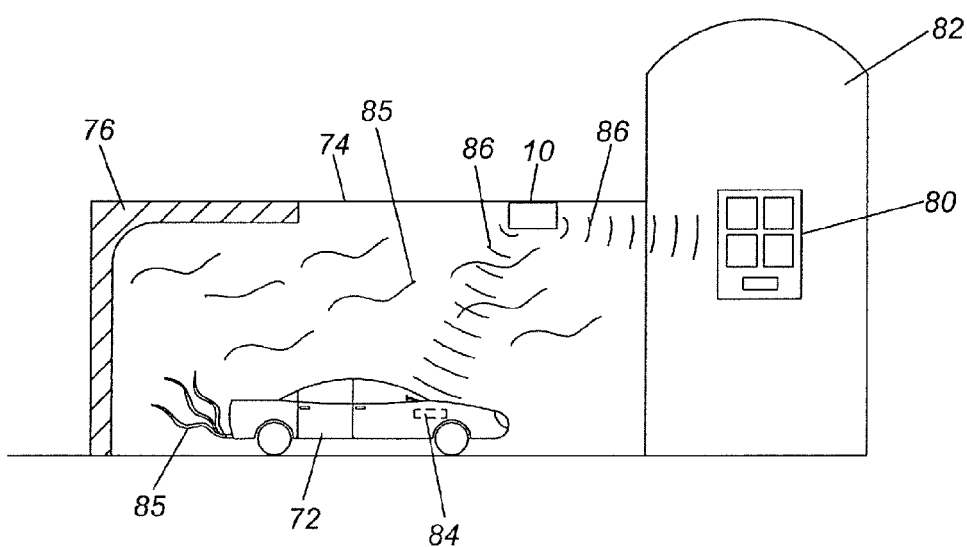
FIG. 8 is a simplified diagram of an illustrative environment for the present invention, illustrating remote signal activation by the programmable carbon monoxide safety device in accordance with the present invention.
Figure 9:
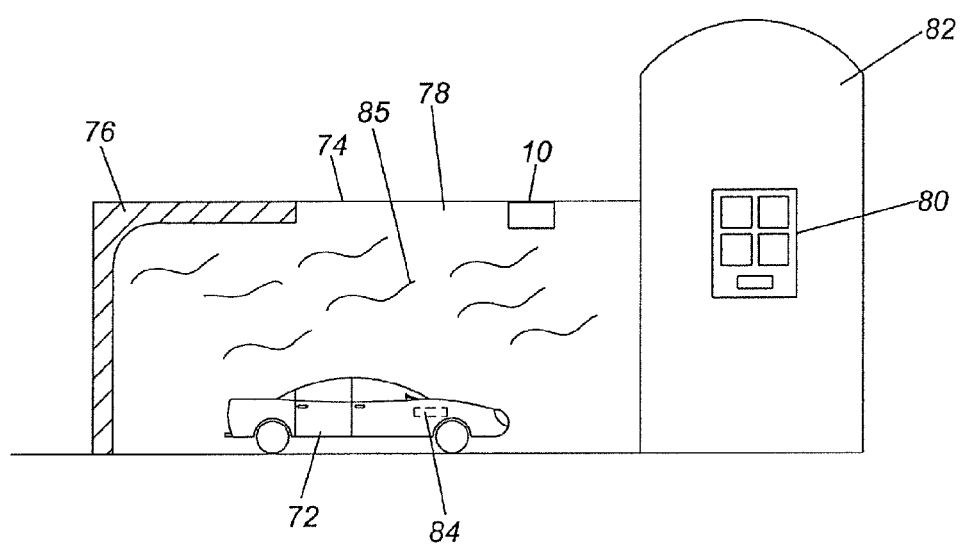
FIG. 9 is a simplified diagram of an illustrative environment for the present invention, illustrating the automobile engine in a deactivated state.

As the automobile 72 continues to run its engine in the enclosed space, the levels of carbon monoxide 85 increase, rising to dangerous levels within the garage 74 as well as in the house 82, see FIG. 7. Should any of the homeowners be sleeping at this time, they are in severe jeopardy of death resulting from carbon monoxide poisoning. To avoid such risk of death, the programmable carbon monoxide safety device 10 responds to the increased levels of carbon monoxide by emitting a command signal 86 to the remote start receiving device 84 and/or to the automobiles electronic control panel to cut off the engine, see FIGS. 8 and 9. The device 10 may send an additional signal 86 to the iPHONE 80, such as an alert message to the user. In addition, the iPHONE may send a signal (not illustrated) to the remote start receiving device 84 and/or the automobile's electronic control panel to cut off the engine either immediately or in a time-delayed manner. The device 10 may also be programmed to be in communication with a subscription based communication/security service such as ON-STAR® or ADT® Security Services, which upon notification of high levels of the gas within the enclosed area may notify the local authorities, activate an alarm within the house, initiate a phone call to the household, or provide remote shut-off. In addition to cutting off the engine, the programmable carbon monoxide safety device 10 may display an audible alarm in hopes of alerting the homeowners of the dangerous carbon monoxide build-up. If levels remain dangerously high, the programmable carbon monoxide safety device 10 may send a signal to the garage door control unit, commanding the unit to open the garage door, thereby venting the area.

Figure 10:
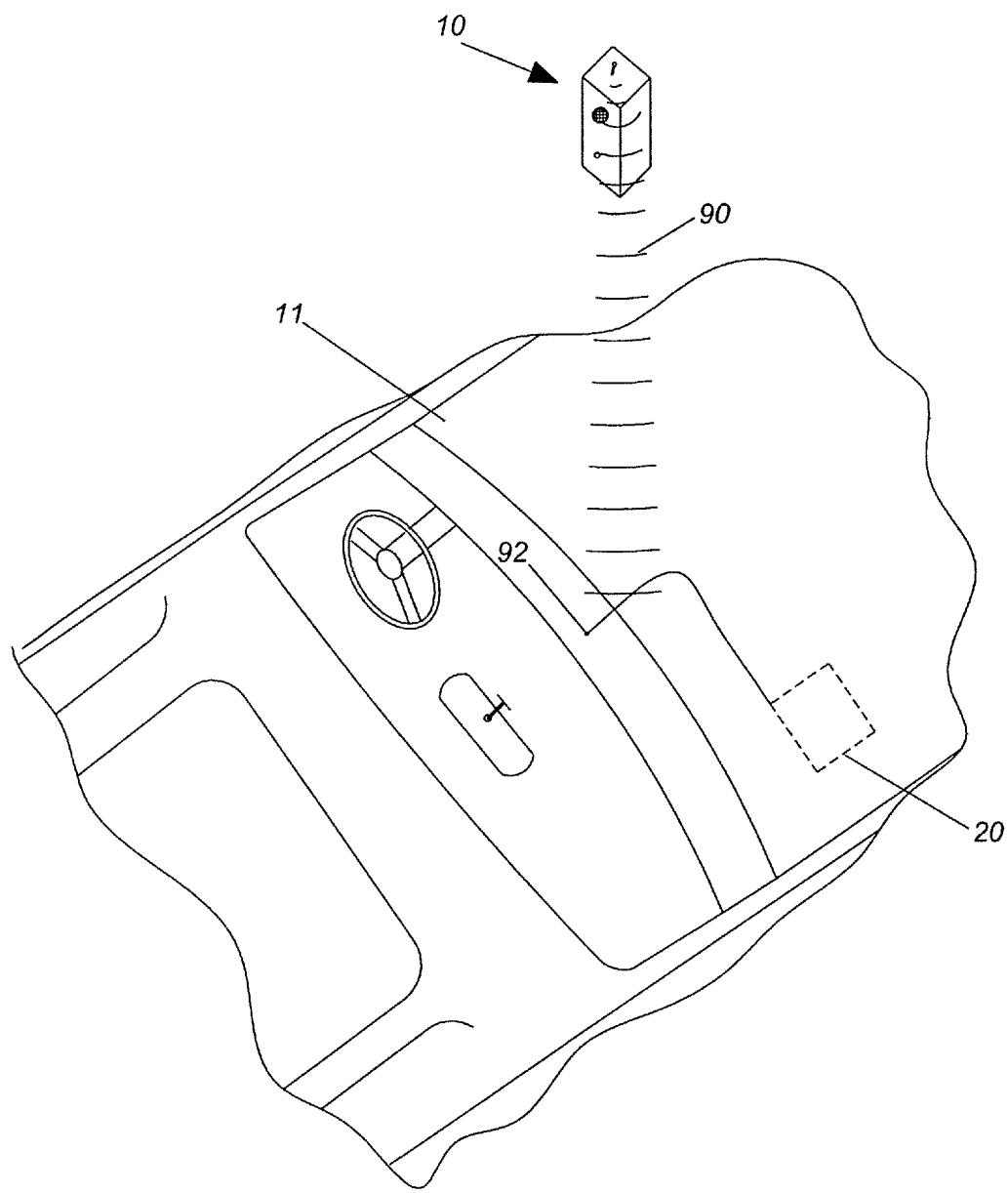
FIG. 10 is a partial perspective view of one embodiment of the present invention, illustrating a vehicle being programmed to respond to signals broadcast by a carbon monoxide detector.

Referring to FIG. 10, an alternative embodiment of the carbon monoxide sensing device 10 is illustrated. In this embodiment, the carbon monoxide detector is hard coded for a particular vehicle 11 in a similar fashion to a key fob or smart key, and thus may be vehicle type and/or make specific. The vehicle's on-board computer 20 is thus programmed to respond to the carbon monoxide detector's distinct digital identity code. This procedure requires the on-board computer 20 of the vehicle to be put into a programming mode which varies from vehicle to vehicle and may need to be completed by a technician. Once the on-board computer has been programmed to save the carbon monoxide detector code and receive signals from the carbon monoxide detector, the on-board computer can be taken out of the programming mode. This embodiment of the carbon monoxide detector 10 is constructed and arranged to emit a radio frequency 90, preferably digital, from a transmitter 24 having an antennae 32 upon determination that a predetermined level of carbon monoxide is present within an enclosed space. So long as the vehicle is within range of the radio frequency, the signal will be received by antennae 92 or the like mounted within the vehicle. Because the antenna is in electrical communication with the vehicle's on-board computer 20, the command from the carbon monoxide detector is transferred to the on-board computer to shut down the engine of the vehicle. Additional commands may also be sent to open the garage door or notify the homeowner via an alarm or similar system connected to the carbon monoxide detector.

Figure 11:
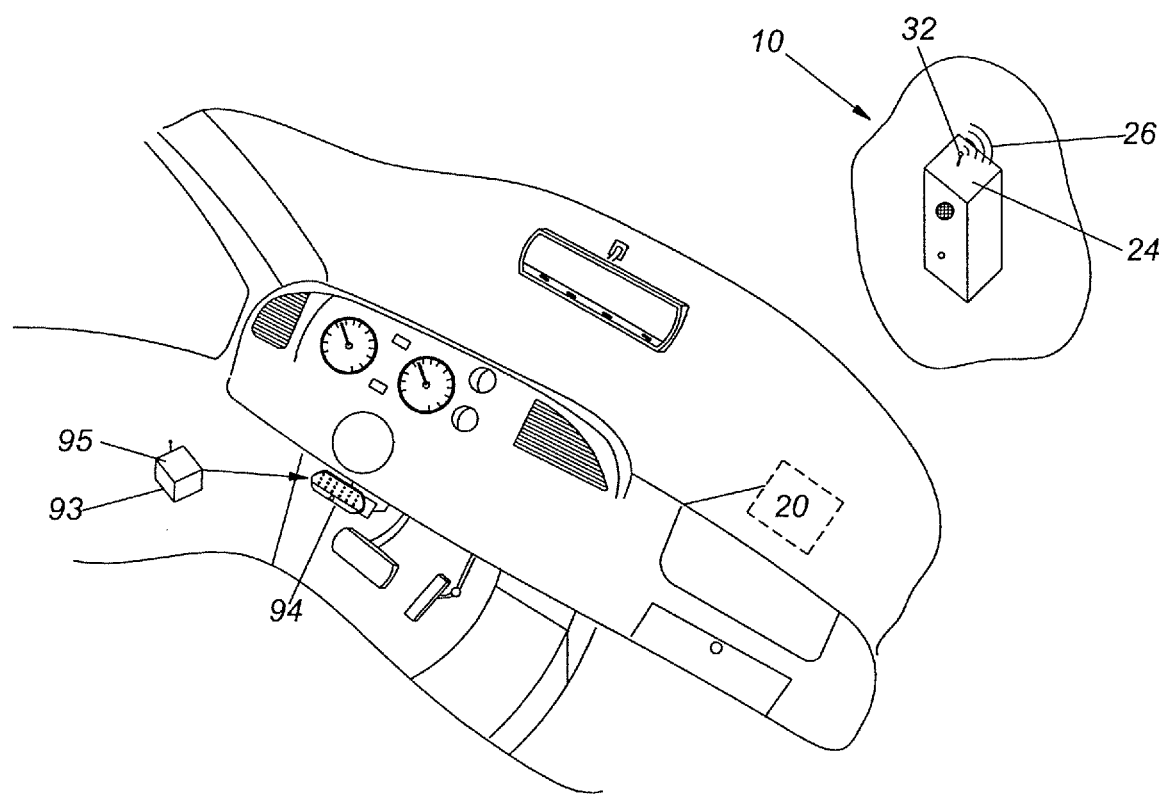
FIG. 11 is a partial perspective view of one embodiment of the present invention, illustrating a communication device adapted for communicating with the on board computer of a vehicle as well as a carbon monoxide detector.

Referring to FIG. 11, an alternative embodiment of the carbon monoxide detector is illustrated. This embodiment of the carbon monoxide detector 10 includes a transmitter/transceiver 24 constructed and arranged for producing command signals 26 to one or more external devices, such as a vehicle network interface 93. The vehicle network interface 93 may connect directly to a J2534 or other suitable connector 94 having access to the vehicular on-board computer system 20. Typically, the command signals 26 are radio frequency signals such as Bluetooth. However, other types of radio frequency signals may be utilized without departing from the scope of the invention. Such radio signals may include, but should not be limited to, RF, Zigby, microwave, infrared, visible light, ultraviolet, x-rays and gamma rays. In addition, signals used by cellular phone technology may be used to transmit the command signals 26 to the vehicle network interface. The command signal preferably contains a unique frequency, code and/or encryption to operate the external device in a secured manner. The transmitter 24 may include an antenna 32 for broadcasting the command signal. The vehicular network interface 93 includes a receiver or transceiver 95 therein that is compatible with the transmitter/transceiver 24 in the carbon monoxide detector 10. This construction allows shut down engine commands to be transferred to vehicles that do not include a smart key, key fob or the like installed by the OEM or aftermarket systems.

Figure 12:
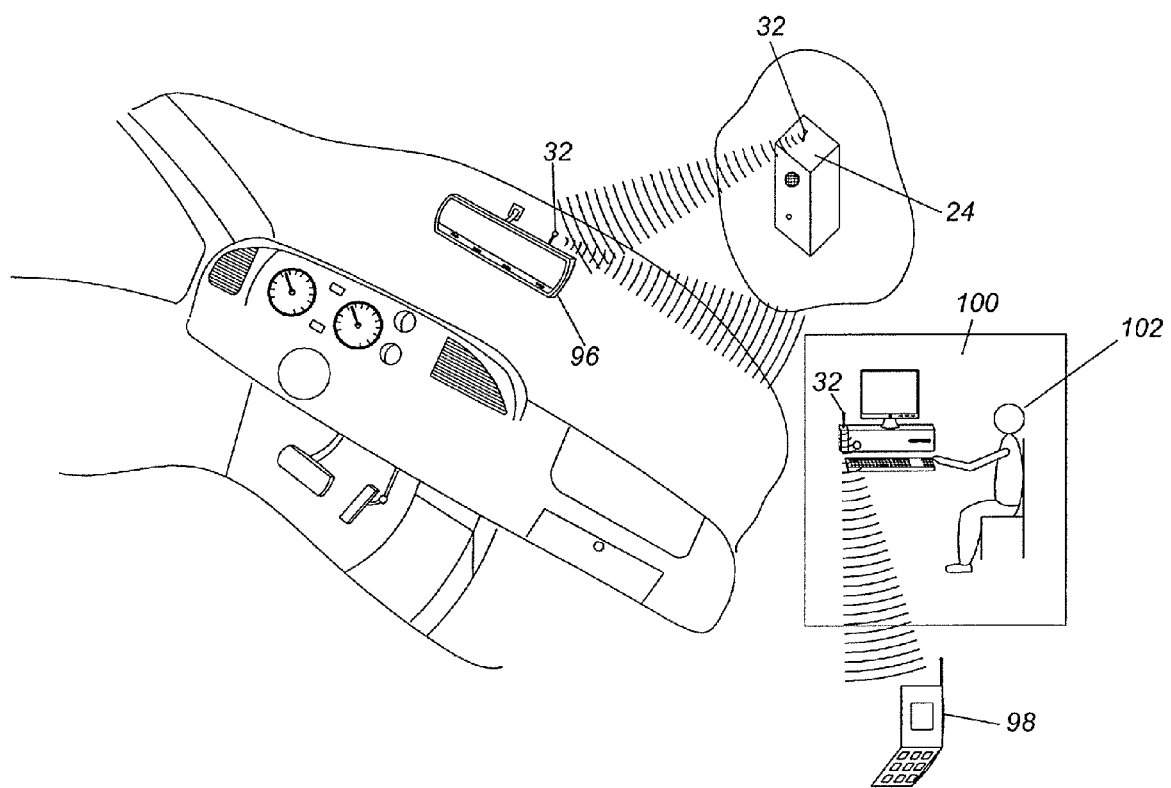
FIG. 12 is a partial perspective view of one embodiment of the present invention, illustrating a carbon monoxide detector in communication with a cell phone type system.
Figure 15:
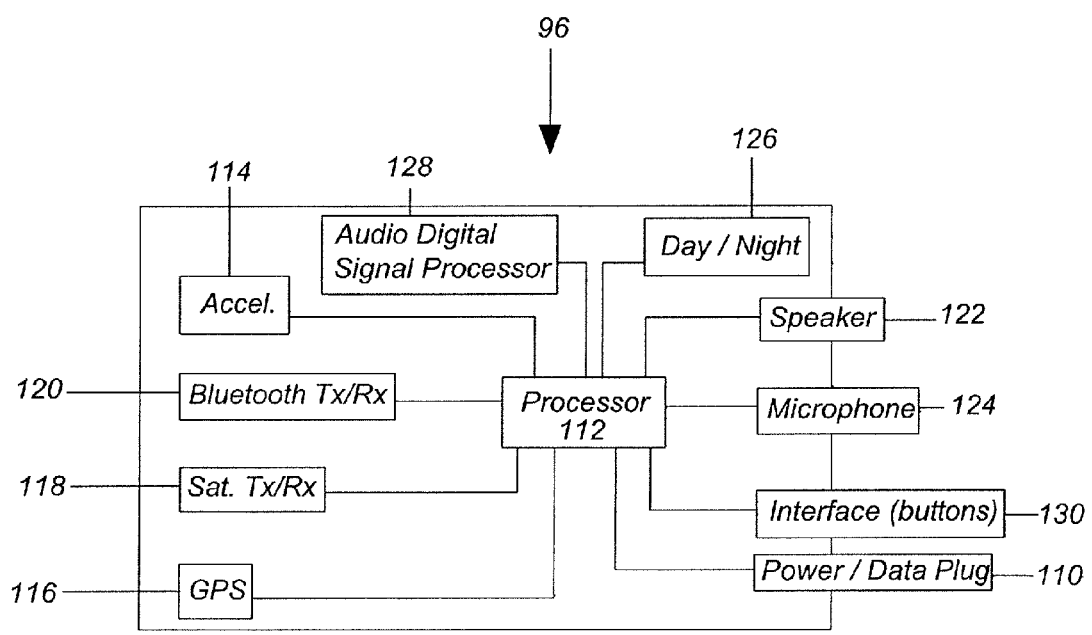
FIG. 15 is a schematic diagram of a typical ONSTAR type satellite/cell network device.

Referring to FIGS. 12 and 15, an alternative embodiment of the present invention is illustrated. In this embodiment, the carbon monoxide detector 10 includes a transmitter/transceiver 24 that can communicate with a satellite/cell network device 96 such as an ONSTAR™ system. A typical ONSTAR satellite/cell network device is incorporated into the rear view mirror of a vehicle and includes a power supply system comprised of a low voltage DC connection within the data plug 110, a computerized data processing system (CPU) with an external multi pin plug 112, an accelerometer 114 that serves as a G-force sensor to detect collisions, a GPS module 116, to determine the vehicles map position, a satellite transmitter/receiver system 118 as a main communication path to and from the centralized On Star customer service center, a Bluetooth receiver/transmitter system 120 to connect a person's cell phone so that the On Star Mirror uses its speaker 122 and microphone 124, an optical day/night sensor 126 (basic photodiode or phototransistor connected to logic), an audio digital signal processor 128 with a speech synthesizer so that data inside the unit can be converted to audible words played through the speaker 122, and user interface buttons 130 with built in data encoded categories. A typical example of the interface button might include pressing the medical symbol button to send data letting On Star know that a medical emergency is the reason for the call. This construction allows for a variety of options relating to locating and shutting down the vehicle as well as providing notice to the vehicle owner that a problem has been detected and action in response thereto may have taken place. The carbon monoxide detector may utilize radio frequency (Bluetooth) to communicate with the satellite/cell network device whereby the satellite/cell network device utilizes a satellite transmitter/transceiver to establish a link to a central office 100. Thereafter, a person 102 in the central office 100 may establish a connection to the vehicular satellite/cell network device 96 or an alternative cell phone device 98 to provide a personal warning relating to the high level of carbon monoxide present where the vehicle is located. Alternatively, if the person in the central office cannot reach the vehicle owner, the GPS feature in the vehicular satellite/cell network device to send emergency personnel to the location of the vehicle.

Figure 13:
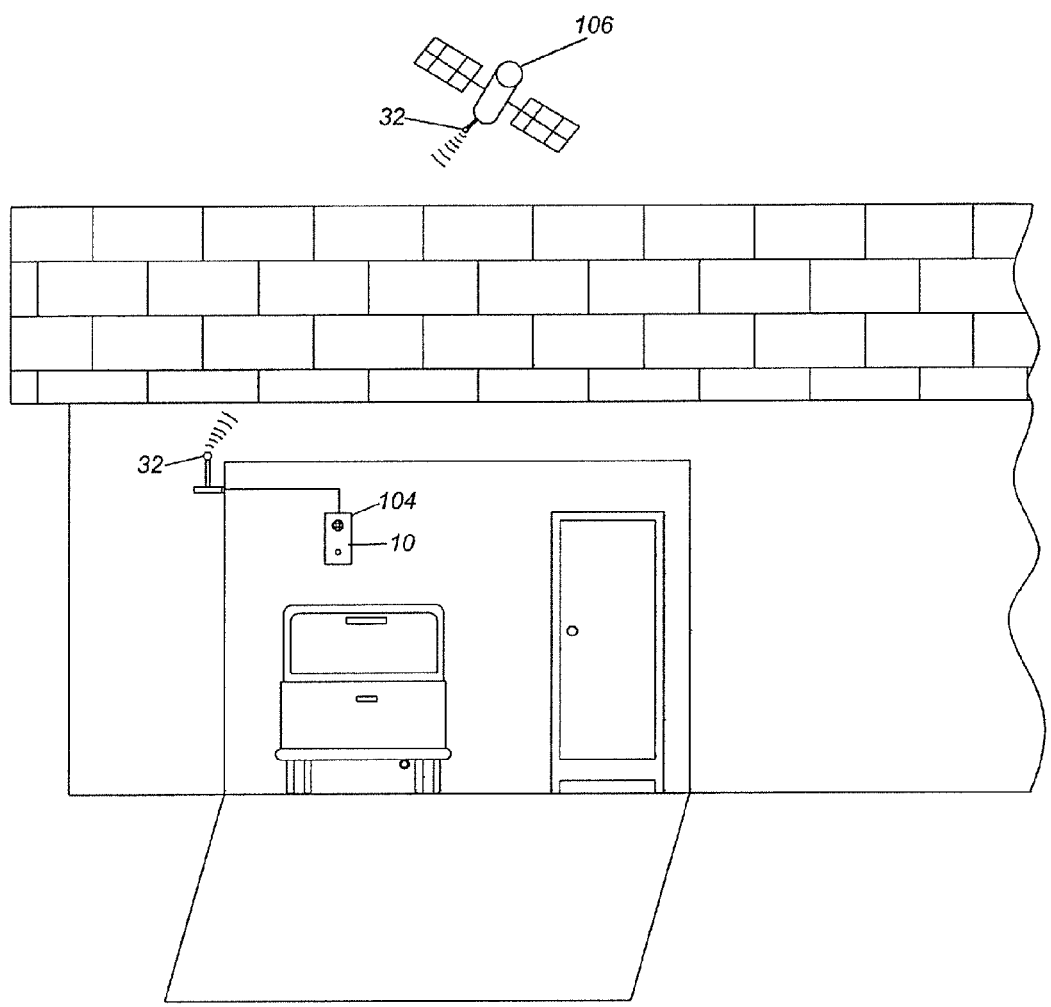
FIG. 13 is a partial pictorial view of one embodiment of the present invention, illustrating a carbon monoxide detector in communication with a satellite type communication system.

Referring to FIG. 13, an alternative embodiment of the carbon monoxide detector is illustrated. In this embodiment, the carbon monoxide detector is equipped with a satellite communication transmitter/transceiver 104. The satellite transmitter/transceiver is attached to an antenna 32 that is constructed and arranged to deliver signals to a satellite 106. The satellite may then transfer the signal to a central office 100 as in the previous embodiment or the signal may be transferred to a cell network or wired phone network whereby notice of the high carbon monoxide level is transferred to a predetermined cell, satellite or wired phone. Alternatively, a GPS system included in the carbon monoxide detector may be utilized to dispatch emergency personnel to the location of the alert.

Figure 14:
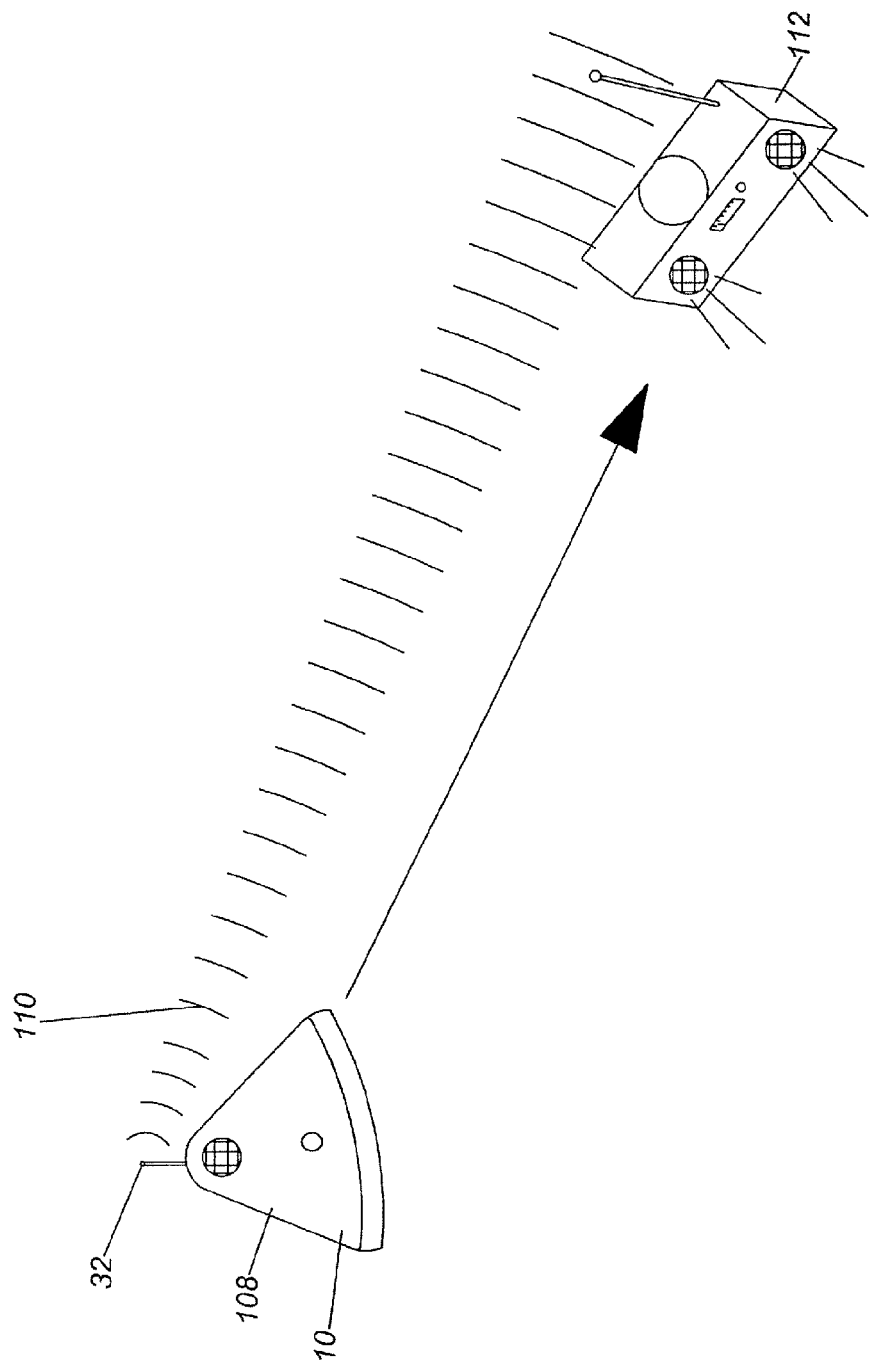
FIG. 14 is a partial pictorial view of one embodiment of the present invention, illustrating a carbon monoxide detector in communication with an FM radio.

Referring to FIG. 14, an alternative embodiment of the carbon monoxide detector is illustrated. In this embodiment, the carbon monoxide detector 10 includes a transmitter 108 that is constructed and arranged to broadcast signals 110 in the FM frequency band in the event carbon monoxide exceeds a predetermined level. In this manner, radios 112 within range of the broadcast signal will receive a warning of the high carbon monoxide level. The signal may include sweeps throughout a range of frequencies to reach the highest number of radios within range.

Figure 16:
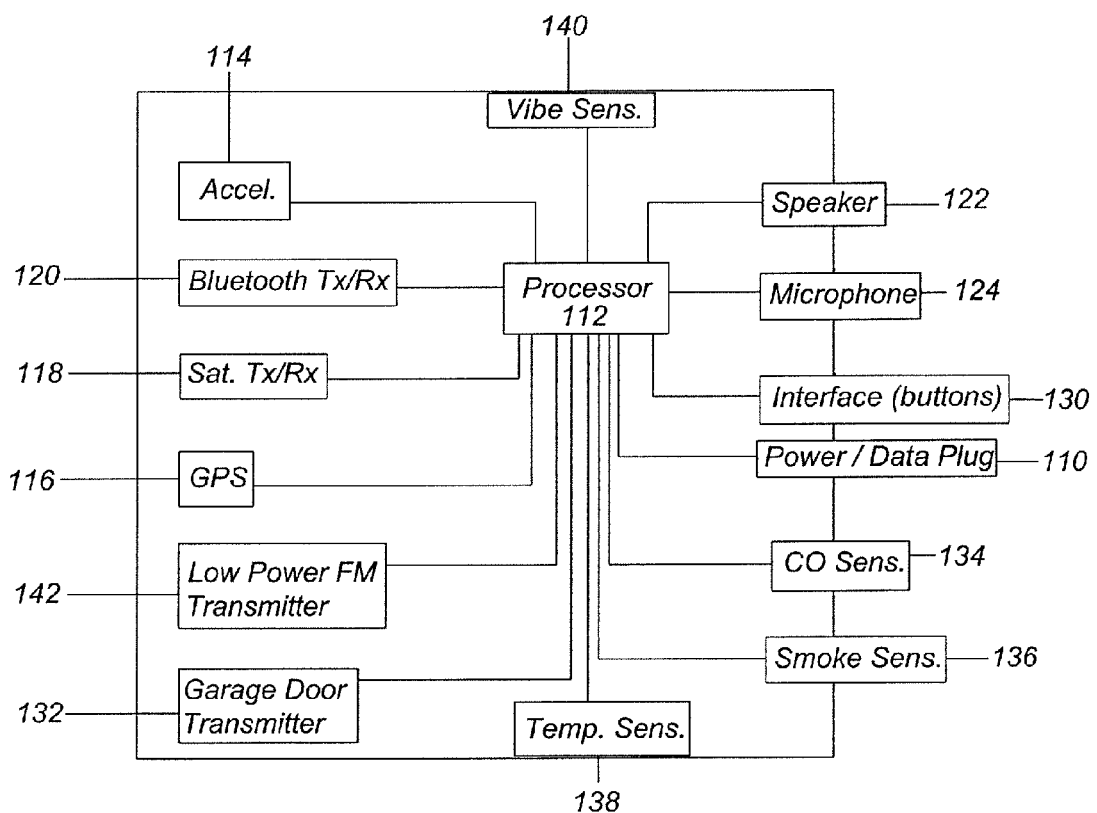
FIG. 16 is a schematic diagram of an improved satellite/cell network device.

Referring to FIG. 16, a schematic of an improved satellite/cell network device 132 is illustrated. This satellite/cell network device is similar in construction to the device shown and described in FIG. 15 with added systems and functionality. The improved system may include a garage door transmitter 132 that may be utilized to open one or more garage doors in response to an exceeded carbon monoxide level as determined by an included CO sensor 134. The satellite/cell network device 132 may also include a smoke sensor 136 and/or temperature sensor 138 that may be utilized in conjunction with the carbon monoxide sensor to determine if the high level of carbon monoxide is due to a fire. The temperature sensor may also be utilized to help an operator at a central location to determine if the vehicle is running by comparing the internal temperature of the vehicle to outside temperature. For example, a temperature sensor inside the mirror would also indirectly indicate data about the car that may be valuable, especially if compared to an outside temperature sensor. For instance, if it's a 96 degree day outside and the car inside sensor is showing 72 degrees, it would be a confirming indicator that the car is running because the AC is on. If a carbon monoxide warning on the aftermarket satellite/cell network device creates a warning call to the satellite provider, that temperature data combined with GPS data could show that someone is sitting in their garage with the car running. In essence, the aftermarket system may have no direct confirmation that the car is running, but the clues from an inside and outside temperature sensor would indicate that the car is running. If however, an internal and external temp sensor indicates approximately the same temp, it would imply that the car is sitting without the air or heat running. Therefore, if a monoxide warning is sent to a satellite service provider, this data combined with GPS data may be valuable. If GPS data indicates the car is parked in a parking garage or public place, it may indicate that another vehicle nearby has been left running unattended. The satellite/cell network device 132 may additionally include a vibration sensor 140 fro an additional indication of the running or not running status of the vehicle. For example, the satellite/cell network device is typically in the form of a rear view mirror. Since the mirror is connected to the windshield it tends to act like a microphone and detect vibration though the glass. A specific vibration signature could be used to determine if the car is running or if a car parked nearby is running. This provides another way to tell if carbon monoxide is coming from the car, or another source nearby such as another vehicle, generator, furnace, etc. Present aftermarket systems rely on the GPS to indicate vehicle movement, therefore low cost temperature sensors and vibration sensors are desirable as secondary indicators to work in conjunction with the monoxide sensors. Another safety feature that may be included is a low power FM transmitter 142 for communicating with the vehicle or other radios located within range of the transmitter to warn those within range of the carbon monoxide. The satellite/cell network device 132 may also work in conjunction with a vehicle network interface 93 (FIG. 11). The vehicle network interface 93 may connect directly to a J2534 or other suitable connector 94 having access to the vehicular on-board computer system 20 for sending and receiving information or command signals to the on board computer system of the vehicle. Typically, the command signals 26 are radio frequency signals such as Bluetooth. However, other types of radio frequency signals may be utilized without departing from the scope of the invention. Such radio signals may include, but should not be limited to, RF, Zigby, microwave, infrared, visible light, ultraviolet, x-rays and gamma rays. In addition, signals used by cellular phone technology may be used to transmit the command signals 26 to the vehicle network interface. The command signal preferably contains a unique frequency, code and/or encryption to operate the external device in a secured manner. The vehicular network interface 93 includes a receiver or transceiver 95 therein that is compatible with the transmitter/transceiver 120 in the satellite/cell network device 132. This construction may allow shut down engine or various other commands to be transferred to vehicles that do not include a smart key, key fob or the like installed by the OEM or aftermarket systems.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A programmable device for detection of toxic gasses comprising:

a controller in electrical communication with a gas sensor, a transmitter and a power source, said controller including a memory for storage of at least one predetermined command;

a gas sensor in electrical communication with said controller, said gas sensor constructed and arranged to sense the concentration of a predetermined gas in the enclosed area, whereby an electrical signal indicative of concentration is transferred to said controller;

a transmitter in electrical communication with said controller, said transmitter constructed and arranged for transmission of coded commands in the form of radio waves;

a power source for supplying electrical power to said controller, said, gas sensor and said transmitter;

said controller receiving electrical signals from said gas sensor, said controller being constructed and arranged to cause said transmitter to transmit said at least one pre-programmed command to an external device upon said controller receiving a signal indicative of said gas concentration exceeding a predetermined level, said external device being a vehicle, said vehicle including a vehicle network interface in electrical communication to a vehicular on-board computer system for sending command signals to said on-board computer system, said vehicular on-board computer system including a learn feature, whereby said vehicular on-board computer can be programmed to respond to said at least one predetermined command.

2. The programmable toxic gas detection device of claim 1 including a receiver for teaching said controller said at least one preprogrammed command, said receiver in electrical communication with said controller and said power source.

3. The programmable toxic gas detection device of claim 2 wherein said receiver is constructed and arranged to receive radio frequency signals.

4. The programmable toxic gas detection device of claim 2 wherein said receiver is constructed and arranged to receive infrared frequency signals.

5. The programmable toxic gas detection device of claim 1 including at least one speaker in electrical communication with said controller and said power supply, said at least one speaker constructed and arranged to deliver an audible sound upon operation of said transmitter.

6. The programmable toxic gas detection device of claim 1 wherein said predetermined command is an engine shut down code for a specific vehicle, said predetermined command being received by the vehicles on board computer for execution.

7. The programmable toxic gas detection device of claim 1 wherein said vehicle network interface cooperates with a J2534 connector of a vehicular on-board computer system.

8. The programmable toxic gas detection device of claim 7 wherein said on board computer programming includes encryption to prevent said on-board computer from responding to unwanted signals.

9. The programmable toxic gas detection device of claim 1 wherein said vehicle network interface is a transceiver.

10. The programmable toxic gas detection device of claim 1 wherein said controller includes a second predetermined command stored therein, said second command configured for communication with a cell phone network, said controller constructed and arranged to transmit said first command signal and said second command signal in an alternating manner upon receipt of said signal indicative of said gas concentration exceeding a predetermined level.

11. The programmable toxic gas detection device of claim 10 wherein said cell network is an on-board vehicular monitoring system, said on-board vehicular monitoring system being constructed and arranged to shut down the internal combustion engine within the vehicle.

12. The programmable toxic gas detection device of claim 1 wherein said controller includes a second predetermined command stored therein, said second command configured for communication with a satellite network, said controller constructed and arranged to transmit said first command signal and said second command signal in an alternating manner upon receipt of said signal indicative of said gas concentration exceeding a predetermined level.

13. The programmable toxic gas detection device of claim 1 wherein said transmitter is an FM transmitter that is constructed and arranged to broadcast signals in the FM frequency band and said at least one predetermined command is a verbal warning of danger, whereby said warning is audible to FM receivers within a predetermined area.

14. The programmable toxic gas detection device of claim 1 including an enclosure surrounding said controller, said transmitter, said gas sensor and said power source, said enclosure constructed and arranged for mounting to a vertical wall surface.

15. The programmable toxic gas detection device of claim 14 wherein said enclosure is mounted on a first side of a wall, a tube extending through said wall to a second side thereof, a first end of said tube open to said second side of said wall, a second end of said tube open to said gas sensor, whereby said gas sensor monitors the concentration of said predetermined gas present at said second side of said wall.

16. The programmable toxic gas detection device of claim 1 wherein said predetermined gas is carbon monoxide.

17. The programmable toxic gas detection device of claim 1 wherein said vehicle network interface in electrical communication to a vehicular on-board computer system includes a global positioning system.

18. The programmable toxic gas detection device of claim 1 wherein said vehicle network interface in electrical communication to a vehicular on-board computer system includes a vibration sensor.

* * * * *